(12) United States Patent
Patzke

(10) Patent No.: US 7,981,597 B2
(45) Date of Patent: Jul. 19, 2011

(54) METHOD FOR PREPARING AGGLUTINATABLE, FIXED PLATELET FRAGMENTS

(75) Inventor: Jürgen Patzke, Marburg (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 959 days.

(21) Appl. No.: 11/898,655

(22) Filed: Sep. 13, 2007

(65) Prior Publication Data

US 2008/0076114 A1    Mar. 27, 2008

(30) Foreign Application Priority Data

Sep. 25, 2006   (DE) .......................... 10 2006 045 550

(51) Int. Cl.
*C12Q 1/00* (2006.01)
*C12Q 1/56* (2006.01)
*G01N 33/554* (2006.01)

(52) U.S. Cl. .............................. 435/2; 435/13; 436/519

(58) Field of Classification Search .......................... None
See application file for complete search history.

(56) References Cited

U.S. PATENT DOCUMENTS 5,185,160 A    2/1993  Chao

FOREIGN PATENT DOCUMENTS

| EP | 1134584 A1 | 9/2001 |
|----|------------|--------|
| WO | WO 01/02853 A2 | 1/2001 |

OTHER PUBLICATIONS

Slezak et al., "Platelet-Mediated Cytotxicity: Role of Anitbody and C3, and Localization of the Cytotoxic System in Membranes", J. Exp. Med. 166 : 489-505 (1987).*
Authi, K.S., "Preparation of Highly Purified Human Platelet Plasma and Intracellular Membranes Using High Voltage Free Flow Electrophoresis and Methods to Study $Ca^{2+}$ Regulation," *Platelets—A Practical Approach*, Chapter 5, pp. 91-109, Oxford University Press, Editors: S.P. Watson and K.S. Authi (1996).
Federici, A.B., et al., "A Sensitive Ristocetin Co-Factor Activity Assay with Recombinant Glycoprotein Ibα for the Diagnosis of Patients with Low von Willebrand Factor Levels," Disorders of Hemostasis, 89(1):77-85 (2004).
Kitaguchi, T., et al., "Characterization of Liposomes Carrying von Willebrand Factor-Binding Domain of Platelet Glycoprotein Ibα: A Potential Substitute for Platelet Transfusion," Biochemical and Biophysical Research Communications, 261:784-789 (1999).
Lee, D.H., et al., "Platelet Substitutes and Novel Methods of Platelet Preservation," *Platelets*, Chapter 60, pp. 915-924, Academic Press, Elsevier Science, Editor: A.D. Michelson (2002).
Abstracts P257-260 from Annals of Hematology, 76(suppl. 1):A92 (1998).

* cited by examiner

*Primary Examiner* — Sandra Saucier
(74) *Attorney, Agent, or Firm* — Finnegan, Henderson, Farabow, Garrett & Dunner, L.L.P.

(57) ABSTRACT

The present invention relates to a method for preparing agglutinatable platelet fragments, in which native platelets are treated with ultrasound and a fixative. The platelet fragments are suitable for use in diagnostic assay methods which include an agglutination reaction, such as, for example, in a method for determining VWF activity.

7 Claims, 2 Drawing Sheets

METHOD FOR PREPARING AGGLUTINATABLE, FIXED PLATELET FRAGMENTS

Figure 1:
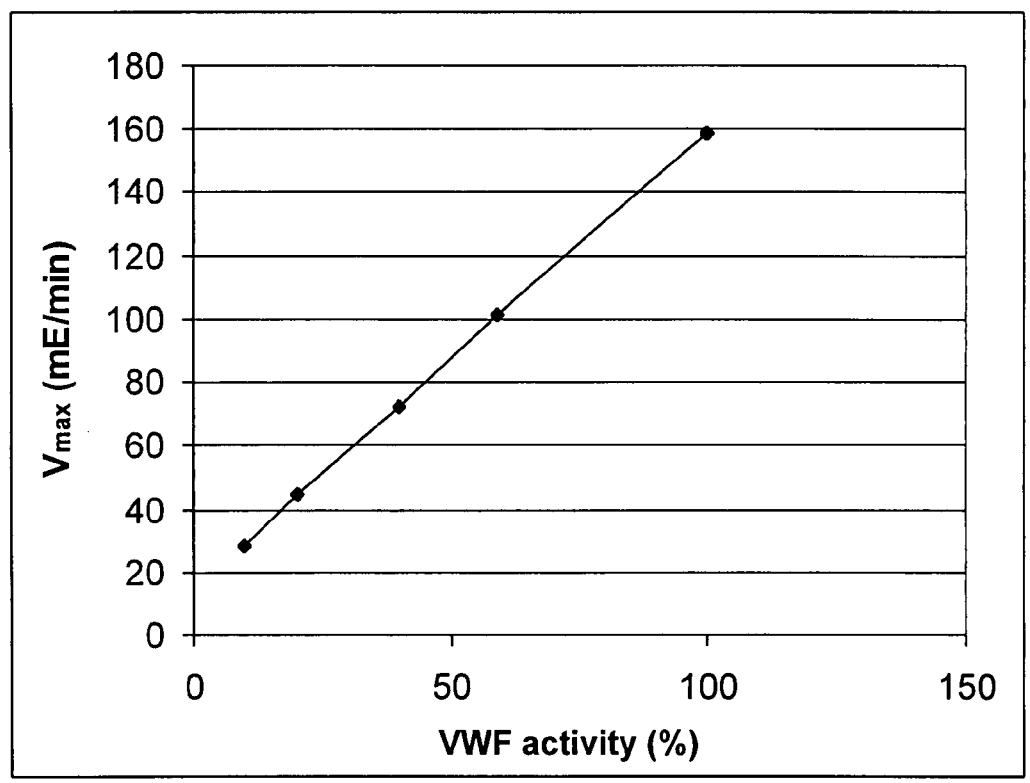

The invention is in the area of diagnosis, especially the diagnosis of coagulation disorders, and relates to a method for preparing agglutinatable platelet fragments and the use thereof in diagnostic test methods which include an agglutination reaction, such as, for example, in a method for determining VWF activity.

von Willebrand factor (VWF) is a high molecular weight, multimeric glycoprotein which has important functions in the process of primary hemostasis. In the event of vascular injury, VWF performs three essential tasks: it mediates the adhesion of platelets to the subendo-thelium, it mediates the aggregation of platelets with one another and thus favors thrombus formation, and it forms with plasma coagulation factor VIII (F VIII) a complex which protects F VIII from premature degradation. Thrombin eliminates F VIII from the F VIII-VWF complex and activates it to F VIIIa, whereby F VIII acquires its procoagulant activity, which is also referred to frequently as F VIII:C.

A von Willebrand syndrome arises due to qualitative or quantitative impairments of VWF and is one of the commonest hereditary bleeding disorders. Various screening methods are available for diagnosing a von Willebrand syndrome, such as, for example, the determination of the bleeding time (BT), quantitative methods for determining the VWF antigen concentration (VWF:Ag) such as, for example, ELISA methods, and methods for determining the VWF activity, such as, for example, the ristocetin-induced platelet agglutination (VWF:RCo).

The method of ristocetin-induced platelet agglutination, which is also referred to as ristocetin cofactor assay, recognizes functional defects in the VWF protein which are not recognized by quantitative methods for determining the VWF antigen concentration. It is therefore necessary for complete diagnosis of a von Willebrand syndrome to carry out a ristocetin cofactor assay to determine the ristocetin cofactor activity. Normally, the ristocetin cofactor assay is carried out by mixing a patient's plasma sample with platelets. Fixed human platelets are normally used for this purpose; however, it is likewise possible to use physiologically active, i.e. native, platelets. Addition of ristocetin is followed by aggregation of the native platelets or agglutination of the fixed platelets as a function of the active VWF present in the sample. The aggregation or agglutination reaction can be detected optically for example by measuring the increase in transmittance and thus makes it possible to quantify the VWF:RCO activity. However, determination of the aggregation or agglutination reaction of whole platelets is associated with some disadvantages.

The first disadvantage is that it is necessary to mix the reaction mixture thoroughly and continuously during the recording of the optical measurement. The continuous thorough mixing is probably necessary in order to increase the frequency of collision of the platelets and thus the reaction rate. Only few of the automated apparatuses employed for the diagnostic tests of hemostasis in the modern laboratory have technical devices allowing such continuous thorough mixing of the reaction mixture during the measurement. Secondly, the imprecision of the conventional ristocetin cofactor assay is relatively high. Since the great majority of automated apparatuses in the area of diagnostic tests of hemostasis is equipped with optical devices which allow only measurement of wavelengths in the visible range, it ought likewise to be possible to evaluate an automated assay method in this wavelength range. When the transmittance is measured following platelet agglutination, only the formation of large aggregates brings about an increase in transmittance in the visible wavelength range. However, the formation of large aggregates, which are moreover susceptible to mechanical destruction, cannot be detected precisely in the normally relatively small assay cuvettes with correspondingly small optical measurement windows. The plots of the platelet aggregation and of the platelet agglutination reactions therefore typically show a considerable scattering in the measurements.

Some alternative assay methods intended to allow more precise determination of the VWF:RCo activity have been developed in the past. In some of these methods, the VWF receptor GP1b or fragments thereof are employed. Thus, for example, ELISA methods which determine the ristocetin-induced binding of VWF to the GP1b receptor have been developed. A method of this type is described for example in Federici, A. B. et al. (Haematologica 2004; 89(1), 77-85) and in WO 01/02853 A2. Another assay format employs particulate support phases such as, for example, latex particles or liposomes (e.g. Kitaguchi, T. et al., Biochem Biophys Res Commun. 1999; 261(3):784-789) to which the GP1b protein is coupled. The GP1b-associated particles are intended to agglutinate in the presence of ristocetin and active VWF.

One disadvantage of the aforementioned methods is the time-consuming and costly preparation of the GP1b-associated solid phases, which is normally preceded by the purification of native or recombinantly expressed GP1b protein. A further necessity—at least for carrying out some assay formats—is for antibodies, e.g. GP1b antibodies, to be available in addition. Overall, the methods are complicated and require the preparation of a number of specific reagents.

The present invention was based on the object of providing a means which can be employed instead of native or fixed platelets in an agglutination assay, and which allows precise photometric determination of the agglutination reaction at wavelengths in the visible range.

It has been found that platelet fragments obtained by a method in which native platelets are initially treated with ultrasound and subsequently fixed have an agglutinability which allows the platelet fragments to be used in an agglutination assay.

Various methods for preparing platelet fragments are known in the state of the art. Platelet fragments are also referred to in the literature as microvesicles or microparticles. The mechanical preparation of platelet membranes, e.g. by ultrasound treatment, freezing/thawing or nitrogen cavitation, results in particles differing in size (Authi, K. S: Preparation of highly purified human platelet plasma and intracellular membranes using high voltage free flow electrophoresis and methods to study $Ca^{2+}$ regulation. Chapter 5 in Platelets—A Practical Approach, 1996, editors Steve P. Watson & Kalwant S. Authi, Oxford University Press, UK and Lee, D. H. & Blajchman, M. A.: Platelet Substitutes and Novel Methods of Platelet Preservation. Chapter 60 in Platelets, 2002, editor Alan D. Michelson, Academic Press, Elsevier Science, U.S.A.). The heterogeneous composition of such preparations makes the use of such platelet fragments in an agglutination assay not very promising, because particles of the same size and having the same surface properties are required. In addition, the known methods are frequently time-consuming and costly, because they include a large number of operations. In many cases, the platelets are incubated with inhibitors in order to avoid excessive activation of the platelets and additionally to protect them from attack by degrading enzymes.

One method for preparing platelet fragments for pharmaceutical purposes is described in U.S. Pat. No. 5,185,160. In this case, the platelets are initially disrupted by repeated freezing and thawing and finally incubated at 60° C. for 20 hours to inactivate possible viral contaminants. The precipitate resulting during the incubation is dissolved by treating the precipitate with ultrasound. After centrifugation of the preparation treated in this way, the supernatant contains the pharmaceutically acceptable platelet fragments which, because of their procoagulant properties, can be used for example for the treatment of patients with a bleeding disorder.

The present invention relates to a method for preparing agglutinatable platelet fragments, where native platelets are initially treated with ultrasound and are fixed after the ultrasound treatment.

The term "agglutinatable platelet fragments" means fragments of platelets which are capable of an agglutination reaction in the presence of active VWF. The agglutinatability of human platelet fragments can be checked for example by mixing the platelet fragments with bovine plasma to give a reaction mixture, the bovine plasma serving as source of bovine VWF. An increase in transmittance of the reaction mixture, with the increase in transmittance preferably being determined with wavelengths from the visible range, is an unambiguous indication of an agglutination reaction taking place and thus of the agglutinatability of the platelet fragments. A possible alternative for checking the aggregatability is to mix the platelet fragments with human plasma and ristocetin to give a reaction mixture.

The platelets used as starting material in the method of the invention may be of animal or human origin. Native platelets can be obtained for example by sedimentation from whole blood or platelet-rich plasma. It is preferred for the platelets to be resuspended before the ultrasound treatment in a buffer solution, e.g. in a phosphate-, TRIS- or imidazole-buffered solution. A platelet suspension preferably used as starting material comprises about 0.5 to $2 \times 10^6$, particularly preferably about $1 \times 10^6$, platelets per microliter.

The buffer in which the platelets are resuspended preferably comprises an anticoagulant. Preferred anticoagulants are sodium citrate, citrate-citric acid glucose, acidic citric acid glucose, EDTA, EGTA, heparin, heparin derivatives, synthetic penta-saccharides such as, for example, fondaparinux, or hirudin. The anticoagulant need not be a constituent of the buffer. It can also be added separately to the platelet suspension.

The ultrasound treatment for fragmenting the native platelets preferably takes place by exposing a suspension of native platelets to sufficiently strong ultrasound. This can take place for example through a high ultrasonic intensity on use of an ultrasonic probe and an appropriately long duration of the treatment. The necessary intensity and duration must be ascertained using the respective ultrasound emitter and the volumes employed. Preferred ultrasound treatments are comparable to an ultrasound treatment carried out with a Branson Sonifier 250 (Branson Danbury, USA) ultrasonic probe with the settings duty cycle: 100%, output control: 7. It is preferred for the platelets or platelet fragments to be continuously cooled, e.g. by storage in an ice bath, before, during and after the ultrasound treatment.

After the ultrasound treatment, the platelet fragments are fixed. The fixation step is advantageously carried out immediately following the ultrasound treatment, i.e. without a time delay. The fixation of the ultrasound-treated platelet fragments preferably takes place by adding a crosslinking fixative to the ultrasound-treated platelet fragment suspension. Examples of particularly suitable fixatives are formaldehyde, paraformaldehyde or glutaraldehyde. In a preferred embodiment of the method, formaldehyde is added in a final concentration of 1% to the ultrasound-treated platelet fragment suspension, and the suspension is incubated at about 2 to 8° C. for about 6 to 16 hours.

In a preferred embodiment, both the ultrasound treatment of the platelets and the subsequent fixation step are carried out in the presence of an anticoagulant. This can be achieved for example by adding an anticoagulant to the platelet suspension before the ultrasound treatment as described above and then, after the ultrasound treatment, adding a fixative without a washing step.

In another preferred embodiment, both the ultrasound treatment of the platelets and the subsequent fixation step are carried out in the absence of a platelet function inhibitor. Platelet function inhibitors, which are preferably not added to the platelet suspension or platelet fragment suspension, include for example cyclooxygenase inhibitors (such as, for example, acetylsalicylic acid), phosphodiesterase inhibitors (such as, for example, theophylline, caffeine, dipyridamole, milfinone, cilostamide, zaprinast), agents which increase the cAMP level (such as, for example, prostaglandin E1, prostaglandin I2, prostacyclin, adenosine), and ADP-degrading enzymes (such as, for example, apyrase).

After the fixation, the fixative is typically removed from the suspension, e.g. by a dialysis, preferably with a phosphate buffer. A dialysis is preferably carried out until the concentration of the fixative in the suspension is less than 0.001%.

In a preferred embodiment, particularly advantageous fractions of the platelet fragments prepared according to the invention are enriched by centrifugation of the platelet fragment suspension. The enrichment can take place by centrifuging the platelet fragment suspension in a first centrifugation step at 1500 g for 10 minutes, and centrifuging the resulting supernatant in a second centrifugation step at 4000 g for 40 minutes. The supernatant is discarded, and the sedimented platelet fragments are resuspended in a buffer solution, preferably a phosphate buffer. The centrifugation steps are preferably carried out at a temperature of about 20° C.

A further embodiment of the method of the invention for preparing agglutinatable platelet fragments includes a further step of the method in which, after the fixation step, GP1b receptor protein is bound to the platelet fragments. GP1b is a glycoprotein which is an integral constituent of the platelet membrane and is involved in the binding of VWF to the platelet surface. The GP1b protein which is bound to the fixed platelet fragments may be native GP1b protein, i.e. that isolated from natural sources such as, for example, from plasma, or recombinantly prepared GP1b protein. In the context of the present invention, the term "GP1b protein" includes both the complete native or recombinant protein and fragments thereof, especially N-terminal fragments which include amino acid residues 1-290 (GP1bαsubunit).

To bind the GP1b protein to the platelet fragments it is possible to use for example one or more antibodies to which the GP1b protein has been coupled and which bind to platelet surface epitopes such as proteins or lipids. Suitable platelet surface epitopes for binding antibodies coupled to GP1b are for example GPIIb, GPIIIa, GPIa, GPVI, phosphatidylcholine and/or phosphatidylserine. It is preferred to use GP1b-coupled antibodies whose GP1b portion is still able to bind VWF. A large number of known methods can be used for coupling GP1b to suitable antibodies. It is likewise possible to use various known methods which enable crosslinking with proteins or other molecules of the platelet fragment surface for stable binding of an antibody-GP1b complex to the surface of the platelet fragments.

The GP1b protein can also be linked chemically to the platelet fragments, or a connection can be produced between the GP1b protein and a molecule of the fragment surface through the use of mediator molecules such as, for example, proteins. For example, the GP1b protein can be coupled to annexin V which binds to phosphatidylserine. Phosphatidylserine is to be found on the surface especially of activated platelets and the fragments produced therefrom. Further examples of mediator molecules are the crosslinker molecules known to the skilled worker, such as, for example, bissulfosuccinimidyl suberate (polyethylene glycol 5), bis-N-succinimidyl pentaethylene glycol ester and many others with which proteins can be linked together. The use of mediator molecules may have the advantageous effect of keeping the GP1b receptor farther away from the surface, thus making it able to bind the VWF more easily.

The present invention further relates to the use of the agglutinatable platelet fragments prepared according to the invention in a method for determining the VWF activity in a sample.

The present invention further relates to a method for determining the VWF activity in a sample, where the sample is mixed with the agglutinatable platelet fragments prepared according to the invention, and the agglutination reaction of the platelet fragments is determined in the reaction mixture. For this purpose, the sample, preferably a plasma sample, is mixed with the platelet fragments, which are preferably suspended in a buffer, to give a reaction mixture. It is additionally possible to add ristocetin to the reaction mixture to determine the ristocetin-dependent VWF activity.

In a particularly preferred embodiment of a method of the invention for determining the VWF activity in a sample, sodium chloride, preferably in the form of an NaCl solution, is added to the platelet fragments shortly before they are mixed with the sample. The NaCl concentration in the platelet fragment suspension after addition of NaCl is preferably below 5 g/l, particularly preferably below 3 g/l.

In a further advantageous embodiment of a method of the invention for determining the VWF activity, the reaction mixture is not continuously mixed. Surprisingly, a continuous mixing of the reaction mixture during the recording of the measurements, such as, for example, by stirring or shaking the assay mixture, is unnecessary because an agglutination reaction allowing quantification of the VWF activity takes place even without continuous mixing of the reaction mixture.

The agglutination reaction of the platelet fragments in the reaction mixture is preferably measured by measuring an optical property of the reaction mixture which changes as a function of the agglutination reaction. The decrease in transmittance or the increase in light scattering is particularly preferably measured.

FIGURES

FIG. 1

The linear increase in the reference curve shows: the behavior of the agglutination reaction of the platelet fragments of the invention is proportional to the VWF activity in bovine plasma.

FIG. 2

Correlation of the assay results (VWF activity) were determined with a conventional platelet assay and with the novel platelet fragment assay for the same bovine plasma samples. The correlation coefficient of $R^2=0.9879$ confirms the linear relation between the assay results in the two assays.

EXEMPLARY EMBODIMENTS

Example 1

Preparation of Agglutinatable Platelet Fragments

Native platelets were obtained by centrifuging a platelet apheresis concentrate from human whole blood in several sample vessels in a precooled centrifuge at 1500 g with brake off at 4° C. for 10 minutes. The supernatants were removed and the sediments were taken up in 30 ml portions of cooled citrate buffer (9.07 g/l disodium hydrogen phosphate, 1.65 g/l potassium dihydrogen phosphate, 0.38% sodium citrate, 1.2 g/l NaCl). The resuspension and homogenization took place with the aid of an Ultra-Turrax disperser (Janke und Kunkel GmbH, Staufen, Germany) (10 sec at 13 500 rpm). The platelet count was then adjusted to 1 000 000 platelets/µl by dilution with citrate buffer.

The platelet suspension was incubated in an ice bath for 30 minutes. Then 20 ml aliquots were treated with a Branson Sonifier 250 (Branson, Danbury, USA) ultrasonic probe with continuous cooling on ice for 15 seconds in the following way: duty cycle: 100%, output control: 7. Immediately thereafter, formaldehyde was added so that the final formaldehyde concentration was 1%. Fixation at 2-8° C. overnight (for about 14 hours) was followed by dialysis with buffer (9.07 g/l disodium hydrogen phosphate, 1.65 g/l potassium dihydrogen phosphate, 1.2 g/l NaCl) until the formaldehyde content had fallen to a concentration of less than 0.001%.

To enrich the particularly advantageous fraction, first the fragment suspension was homogenized by using the Ultra-Turrax disperser, and then 20 ml aliquots were centrifuged at 1500 g at 20° C. for 10 minutes. The supernatants were removed and centrifuged at 4000 g at 20° C. for 40 minutes. The sediments were taken up in 1 ml portions of phosphate buffer (0.907 g/l disodium hydrogen phosphate, 0.165 g/l potassium dihydrogen phosphate) and treated with a shaker until the sediment was completely detached from the base. Several sediments resuspended in this way were combined in a 14 ml plastic tube and homogenized using an Ultra-Turrax disperser at 13 500 rounds/minute for 5 to 10 seconds.

Immediately before use of the fragment suspension for determining the VWF activity, NaCl was added so that the NaCl concentration in the suspension was 2 g/l.

Example 2

Determination of the VWF Activity in Bovine Plasma Using the Platelet Fragments Prepared According to the Invention The following steps were carried automatically in a BCT® (Dade Behring Marburg GmbH, Marburg, Germany) coagulation analyzer:

50 µl of platelet-poor bovine citrated plasma were mixed with 100 µl of a platelet fragment suspension prepared as in example 1 to give a reaction mixture, and incubated at 37° C. for 15 seconds.

The extinction of the reaction mixture at 620 nm was measured over a period of 90 seconds without mixing the reaction mixture during the measurement. The kinetics found in this way for the aggregation reaction were used to determine the change in extinction (mE/minute), and the maximum change in extinction (Vmax of the increase in extinction) was found.

A calibration plot was constructed by diluting normal bovine plasma (VWF activity=100%) with VWF-deficient plasma in a dilution series. The undiluted normal plasma, and the various dilutions having different VWF activities, were analyzed by the method described. FIG. 1 shows the reference plot constructed in this way. The behavior of the agglutination reaction of the platelet fragments of the invention is proportional to the VWF activity of a sample.

Figure 2:
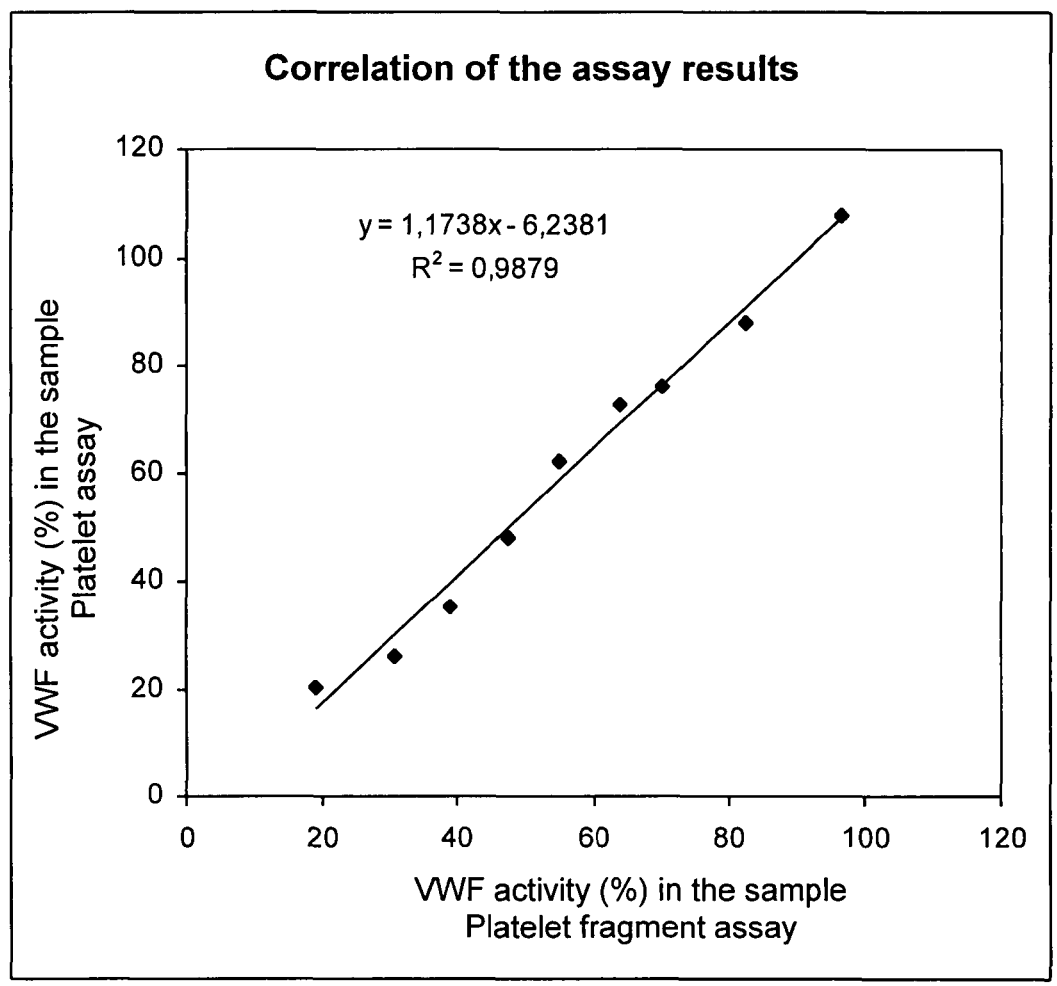

In a comparative experiment, the same bovine plasma dilutions were assayed in a conventional agglutination assay in which fixed whole platelets were mixed with the sample. As is evident from FIG. 2, the results of the novel assay method using the platelet fragments prepared according to the invention correlate very well with the assay results from the conventional assay.

The invention claimed is:

1. A method for preparing agglutinatable platelet fragments comprising,
    (a) treating a suspension of native platelets with ultrasound to fragment the platelets, and then,
    (b) adding a fixative to the suspension of platelet fragments from step (a).

2. The method as claimed in claim 1, further comprising adding an anticoagulant to the suspension of native platelets before treating with ultrasound in step (a).

3. The method as claimed in claim 1, wherein steps (a) and (b) are performed in the absence of platelet function inhibitors.

4. The method of claim 3, wherein the platelet function inhibitor is chosen from acetylsalicylic acid, theophylline, caffeine, dipyridamole, milfinone, cilostamide, zaprinast, prostaglandin E1, prostaglandin I2, prostacyclin, adenosine, and apyrase.

5. The method as claimed in claim 1, wherein the platelets are fixed after the ultrasound treatment with a fixative chosen from formaldehyde, paraformaldehyde, and glutaraldehyde.

6. The method as claimed in claim 1, further comprising
    (c) binding GP1b receptor protein to the suspension of fixed platelet fragments from step (b).

7. The method of claim 6, wherein the GP1b receptor protein is coupled to an antibody that binds to a platelet surface epitope.

* * * * *